United States Patent [19]

Yang et al.

[11] Patent Number: 5,024,933

[45] Date of Patent: Jun. 18, 1991

[54] METHOD AND KIT FOR SAMPLE ADHERENCE TO TEST SUBSTRATE

[75] Inventors: Huey-Lang Yang, Tenafly, N.J.; John Todd, Mundelein, Ill.; Huey-Ling L. Jou, Harrison, N.J.

[73] Assignee: Enzo Biochem, Inc., New York, N.Y.

[21] Appl. No.: 192,256

[22] Filed: May 10, 1988

[51] Int. Cl.$^5$ .................. C12Q 1/68; G01N 1/00; G01N 1/28

[52] U.S. Cl. ..................... 435/6; 436/174; 436/175; 435/810

[58] Field of Search .................. 436/174, 521–527, 436/175; 525/54; 435/6, 810

[56] References Cited

U.S. PATENT DOCUMENTS 4,668,637  5/1987  Guesdon et al. ............ 436/521
4,908,404  3/1990  Benedict et al. ............ 525/54.11

OTHER PUBLICATIONS

Kaleem et al., *Nature*, vol. 325, pp. 328–329, 1987.
Thiebaut et al., *PNAS*, vol. 84, pp. 7735–7738, Nov. 1987.
Engel, *American Biotechnology Laboratory*, Jun. 1988.

*Primary Examiner*—David L. Lacey
*Assistant Examiner*—Jan M. Ludlow
*Attorney, Agent, or Firm*—Elaine P. Brenner; Ronald C. Fedus

[57] ABSTRACT

Disclosed is an improvement relating to adhesion of samples onto a surface for nucleic acid hybridization assay to detect a target polynucleotide. In one aspect, the invention provides a method of adhering a tissue, cell or other target polynucleotide-containing sample to a substrate under nucleic acid hybridization assay compatible conditions. In another aspect, the method comprises a hybridization assay procedure. Also disclosed are kits for performance of such procedures.

32 Claims, No Drawings

METHOD AND KIT FOR SAMPLE ADHERENCE TO TEST SUBSTRATE

BACKGROUND OF THE INVENTION

1. Field of the Invention

This invention relates to the adhesion of tissue, cell or other polynucleotide-containing samples to analytical elements or devices for nucleic acid hybridization assay testing. More particularly, it relates to the use of naturally occuring adhesive substances in solid state hybridization assay testing of such samples for clinical diagnostic or research purposes.

2. Brief Description of the Prior Art

Histology, cytology and related fields have long used stained or unstained tissue sections for a wide variety of educational, experimental and clinical applications. Both paraffin and frozen tissue sections or cell samples, such as from blood or cervical lavage, are attached onto glass slides for microscopic examination.

One important aspect of these procedures is the reliability of the adherence of nucleic acids, cells and tissue sections to the underlying slide or other surface on which the examination is performed. A recurring problem, particularly for in situ hybridization assays, has been failure of adherence of the cells or tissue section to the slide. Treatment with, for example, HCl, $H_2O_2$, proteinase digestion, prehybridization and hybridization at elevated temperatures or with formamide all can cause cell or tissue release. The cell digestion by proteinase K as part of the sample preparation for in situ hybridization assays has amplified the problem, even when extremely dilute preparations of the proteinase are used. See, for example, Morley, et al., *In Situ Localization of Amylase mRNA and Protein. An Investigation of Amylase Gene Activity In Normal Human Parotid Cells*, J. Histochem. and Cytochem., 35:9–14(1987) and Brigati, et al., *Detection of Viral Genomes In Cultured Cells and Paraffin-Embedded Tissue Sections Using Biotin-Labeled Hybridization Probes*, Virology, 126:32–50(1983).

Some of nature's most powerful adhesives are produced by sessile intertidal marine invertebrates such as mussels and the efforts to correlate adhesiveness of *Mytilus edulis* through disc-tipped threads termed "byssus" with some chemical composition has been hindered by the extreme insolubility of the disc proteins. This adhesive disc has been referred to by histologists as the "phenol gland" because of its storage of aromatic or "polyphenolic protein".

Waite, et al., *The Bioadhesive of Mytilus Byssus: A Protein Containing L-Dopa*, Biochem. Biophys. Res. Comm., 96:1554–1561(1980) report here that the adhesive disc and the polyphenolic protein of *Mytilus* contain significant amounts of L-3,4-dihydroxyphenylalanine (L-DOPA). Extensive isolation procedures are reported. An aromatic compound "A" was detected in hydrolysates and was said to be identical with standard L-DOPA based on several analytical criteria. Although the authors acknowledge that the function of DOPA in the disc protein is not known, they raise the question of whether DOPA confers unique adhesive properties on the disc protein and/or contributes to the interaction of collagen and polyphenolic protein.

Waite, et al., *Polyphenolic Substance of Mytilus edulis: Novel Adhesive Containing L-DOPA and Hydroxyproline*, Science 212:1038–1040 (1981) report that the adhesive discs of *Mytilus edulis* are rich in the amino acid 3,4-dihydroxyphenylalanine (dopa). An acid-soluble protein was extracted and purified from the phenol gland located in the byssus-secreting foot of the animal. This protein was found to be highly basic and to contain large amounts of lysine, dopa, and 3- and 4-hydroxyproline (hyp). The authors conclude that this protein contributes to byssal adhesion.

Waite, *Evidence for a Repeating 3,4-Dihydroxyphenylalanine-and Hydroxyproline-containing Decapeptide in the Adhesive Protein of the Mussel, Mytilus edulis L.*, J. Biol. Chemin., 258:2911–2915(1983). Here, treatment of the adhesive protein with clostridial collagenase was reported to reduce the molecular weight by less than 10%. The collagenase-resistant fragment was reported to contain most or all of the Hyp and Dopa. Trypsin treatment of the polyphenolic protein was reported to result in extensive degradation. The major tryptic peptide (80%) contains 10 amino acids including Hyp and Dopa and was shown by sequence analysis to be $H_2N$-Ala-Lys-Pro-Ser-Tyr-Hyp-Hyp-Thr-Dopa-Lys-COOH.

When the organism is placed on glass, the attachment plaques are reported to exhibit a mean adhesive tensile strength of $10^6$ newton-meter$^{-2}$. The substance in the plaque mediating adhesion between the collagenous threads of the disc and the substrate is stated to be the polyphenolic protein. The authors mention that polyphenolic protein has attracted attention as an adhesive since, unlike most synthetic adhesives, its performance, polymerization, and longevity are not adversely affected by the presence of water. Although the reason for this resistance to water is reported to be unknown, it is speculated as likely related to the unusual composition of the polyphenolic protein.

Waite, U.S. Pat. No. 4,496,397 discloses a method for purifying polyphenolic proteins rich in catechol, such as those from *Mytilus edulis* and stabilizing them in a range of pH from 7.0 to 9.0. The described method includes the additional steps, after acetic acid extraction of the catechol-containing protein, of removing low molecular weight acid soluble materials from the extract and reacting the extract fraction with a water soluble borate.

Waite, U.S. Pat. No. 4,585,585 discloses methods for the preparation and isolation of decapeptides having the formula ala-lys-pro/hyp-ser/thr-tyr/dopa-pro/hyp-pro/hyp-ser/thr-tyr/dopa-lys and large polyphenolic molecules comprising repeating units of the decapeptide for which the linking groups are amino acids, oligopeptides or bifunctional spacers. Digestion of the polyphenolic proteins in trypsin in the presence of a neutral or slightly basic buffer results in the above decapeptides. The specification states that the decapeptides can be used as building blocks in the construction of larger polyphenolic molecules possessing the adhesive capabilities of the native bioadhesive protein.

When the bioadhesive proteins are treated with clostridial collagenase, the molecular weight is reduced to between about 110,000 and about 130,000. The resultant collagenase-resistant fragments contain most of the HYP and DOPA of the original bioadhesive proteins. Collagenase-resistant fragments are rapidly degraded by trypsin into decapeptides, the repeating unit in the native protein. Alternatively, trypsin digestion may be performed on isolated bioadhesive proteins, without first treating the bioadhesive proteins with clostridial collagenase.

Waite, U.S. Pat. No. 4,687,740 issued from a divisional application of the above U.S. Pat. No. 4,585,585 and relates to the method of preparation of the decapeptide.

A product referred to as Cell-Tak cell and tissue adhesive is available from BioPolymers, Inc. of Farmington, CT and is said to be a highly purified formulation of the adhesive protein of the marine mussel. The use for which it is offered is for cell and tissue culture growth under conditions which are compatible with and encourage cell viability and proliferation.

Since the detection of the adhesive property in the acid-soluble fraction as described in the earlier reports identified above subsequent and recent developments as disclosed in the cited patents, demonstrate that the direction of the field has been toward complete purification, leading to synthetic decapeptides and the synthetic construction of large polyphenolic proteins therefrom. Further, application of these purified and synthetic proteins has been directed toward physiologically favorable conditions, such as those in which not only the cell or tissue culture are to be grown but also the protein itself are not exposed to potentially destructive harsh conditions.

BRIEF SUMMARY OF THE INVENTION

In contrast to anything that would be suggested by the efforts described above or from a general knowledge of the environmental conditions proteins require for structural integrity, let alone activity, it has been discovered, in accordance with the present invention, that an isolate of the naturally occurring mussel adhesive protein is highly effective at maintaining adherence of tissue, cell and other polynucleotide-containing samples to surfaces onto which they are fixed even throughout the harsh and stringent conditions of the pretreatment steps necessary for nucleic acid hybridization assays. These include exposure to highly elevated temperatures, strongly acidic environments and harshly toxic reagents, such as formamide.

Accordingly, the present invention provides an improvement relating to adhesion of samples onto a surface for nucleic acid hybridization assay to detect a target polynucleotide. In one aspect, the invention provides a method of adhering a tissue, cell or other target polynucleotide-containing sample to a substrate under nucleic acid hybridization assay compatible conditions. This method comprises (a) depositing onto at least a portion of a surface on which said nucleic acid hybridization assay is to be performed an adhesive composition which includes an isolate of a naturally occurring mussel adhesive protein; (b) adhering said sample onto at least a portion of the surface onto which said adhesive composition has been deposited; and (c) treating said adhered sample so as to establish conditions compatible with performance of a nucleic acid hybridization thereon. The treatment step can include cells in the sample so as to expose the nucleic acid contents thereof for hybridization, digesting with proteinase, fixing the sample to the substrate and exposing the sample to chemicals and reagents including formamide and strong acids.

In another aspect, the invention relates to a nucleic acid hybridization assay perfomed on a substrate to which is adhered either a target polynucleotide sample or at least one reagent for the assay. This method comprises (a) depositing an adhesive composition which includes an isolate of a naturally occurring mussel adhesive protein onto at least a portion of a surface on which a nucleic acid hybridization assay is to be performed on a sample; (b) adhering onto at least a portion of the surface onto which the adhesive composition has been deposited a target tissue, cell or polynucleotide sample or a composition that is adhesive to the surface and includes an oligo- or polynucleotide specifically hybridizable with a first portion of the target; (c) contacting the polynucleotide of (b), under hybridization assay conditions, with (i) a reagent composition comprising a detectably labeled oligo-or polynucleotide specifically hybridizable with at least a portion of the target when the target is adhered to the surface or (ii) the target and a reagent composition comprising a detectably labeled oligo- or polynucleotide specifically hybridizable with a second portion of the target when the oligo- or polynucleotide hybridizable with the first portion of the target is adhered to the surface; and (d) detecting any response thereto.

The target polynucleotide is usually a double-stranded DNA or RNA molecule of human, animal, microbial, plant or viral origin. The adhesive composition principally comprises as the adhesive component thereof an acid-soluble isolate of the naturally occurring mussel adhesive protein from a mussel of the genus *Mytilus*. The surface is at least one surface of a dimensionally stable analytical device, such as a microscope slide.

In another aspect, the invention provides an improvement relating to adhesion of cell and tissue samples onto analytical elements or slides in a nucleic acid hybridization assay kit. The kit comprises at least one analytical element having on at least one surface thereof an adhesive composition which includes an acid-soluble isolate of a naturally occurring mussel adhesive protein and at least one reagent container having therein a reagent composition comprising a detectably labeled oligo- or polynucleotide which is specifically hybridizable with the target polynucleotide and which, when so-hybridized therewith, directly or indirectly produces a detectable response.

The adhesive composition is prepared by obtaining phenolic glands from *Mytilus edulis*, preparing a first homogenate of them in a neutral or alkaline solution, separating out and recovering a tissue pellet from it, mixing the pellet with a mild acid solution, such as acetic acid, to produce a second homogenate, separating out and recovering the supernatant from the second homogenate, and concentrating the adhesive composition from the supernatant.

DETAILED DESCRIPTION OF THE INVENTION

Various features and alternative aspects of the method whereby the adhesive composition which includes an essentially unpurified isolate of a naturally occurring mussel adhesive is prepared are as follows.

Phenolic glands are obtained from *Mytilus edulis* using procedures which have been described in the literature. A first homogenate of the phenolic glands is prepared in water or a neutral or mildly alkaline solution. Tris or other neutral buffers are suitable. Separation of the formed and soluble fractions of the first homogenate, so as to produce a tissue pellet, can be performed, for example, by centrifugation.

The pellet which is recovered is mixed or blended with a solution of a mild acid, such as acetic acid, to produce a second homogenate. This solution can also optionally include phenylmethylsulfonyl fluoride that serves as a protease inhibitor. Separation of the second homogenate and recovery of the supernatant, can be performed, for example, by centrifugation.

Concentrating the adhesive composition from the supernatant can be performed using various procedures, including dialysis with sephadex, sepharose or polyethylene glycol, by ammonium sulfate precipitation, or by lyophilization.

The surface on which the adhesive is coated is typically a glass microscope slide or similar material. The hybridization assay can be performed on any suitably shaped surface onto which the adhesive protein has been applied. The adhesive composition is preferably present in a volume of from about 0.5 ul to about 5.0 ul sufficient to cover 15×15 millimeters of surface with the solution concentration adjusted to predetermined optimal conditions.

After the tissue is attached, the sample is then subjected to hybridization with the reagent. The target polynucleotide can be attached to the analytical surface by the adhesive composition, either in the form of bare nucleic acid or a tissue section in which the nucleic acid content has been rendered single-stranded and accessible by cell disruption. More than one labeled probe can be used to identify target oligo- or polynucleotides of interest. Suitable labels include, but are not limited to avidin, streptavidin, biotin, iminobiotin, an electron dense component, a magnetic component, an enzyme, a hormone component, a radioactive component, a metal-containing component, a fluorescing component, and an antigen or antibody component or combinations thereof. The reagent composition can include oligo- or polynucleotides which are both labeled or unlabeled. Alternatively, the analytical surface can have attached thereto by the adhesive a composition that includes an oligo- or polynucleotide specifically hybridizable with a first portion of the target polynucleotide. In this case, an additional reagent is provided which comprises a detectably labeled oligo- or polynucleotide specifically hybridizable with a second portion of said target.

The following examples illustrate, but do not limit the scope of the invention.

EXAMPLE I

This example describes the isolation and preparation of the adhesive mussel protein preparation in accordance with the invention (M-Protein) from *Mytilus edulis*.

REAGENT PREPARATION

M-Protein, Solution A

The preparation of 1 liter of M-protein solution A is as follows. To a 2 liter glass beaker with magnetic stir bar, are added the following:

| | |
|---|---|
| 58.45 g | NaCl |
| 6.06 g | Tris base |
| 7.90 g | EDTA |
| 1.25 g | Ethylmaleimide |
| 0.065 g | KCN |

Then, phenylmethylsulfonylfluoride (0.174 g.) is dissolved in isopropyl alcohol(1 ml), and added to the solution prepared above. Adjustment to pH 7.5 with HCl, and adjustment of volume to 1 liter are made, if nescessary.

M-Protein, Solution B(0.9M Acetic Acid.

Deionized $H_2O$ (500 ml) is added to an appropriate vessel with a magnetic stir bar. With the stir bar stirring, glacial acetic acid (54 ml) is slowly added. The volume is corrected to 1 liter with deionized water and the solution is stored in a tightly capped container.

PREPARATION OF MUSSELS

Twenty pounds of mussels are obtained the same day they are to be processed and are kept on wet ice. Working rapidly, the phenolic gland is excised and immediately placed on a piece of dry ice. The frozen phenolic glands are collected in a sterile 50 ml polypropylene test tube which is maintained on dry ice.

ISOLATION OF M-PROTEIN

Frozen Mussel phenolic glands are blended in a blender with an Eberbach top with a minimal volume of chilled M-Protein Solution A (150-200 ml). The resulting consistency should approximate that of a milkshake. Keeping the mixture chilled, it is transferred to a chilled tissue homogenizer, such as a Dounce homogenizer, and ground on ice until the mixture is free of lumps. The mixture is then poured into chilled, 25 ml ultracentrifuge tubes and spun in a precooled (0°-8° C.) ultracentrifuge at 40,000 RPM for 1 hr. Supernatants are discarded. Pellets are transferred to a blender and a minimal amount of chilled M-Protein Solution B (50-100 ml) is added. This is blended for 1 minute, poured into chilled ultracentrifuge tubes and spun for 1 hour at 40,000 RPM. The supernatants are pooled and the pellets are discarded. The pooled supernatant is introduced into dialysis bags (75 ml/bag). The bags are sprinkled with Sephadex G 150 to concentrate the protein and stored at 0°-8° C. overnight during which the volume should decrease by at least 90%. Tissue specimen sections are applied and tested as described below.

EXAMPLE II

This example describes the preparation of an analytical device incorporating the adhesive composition of the invention and other materials for nonisotopic nucleic acid hybridization assay of tissue.

A standard microscopeslide staining holder set such as that available from American Scientific Products, Edison, N. J.; Catalog No. S7626-12 or equivalent, and a compatible slide staining holder such as that available from American Scientific Products, Edison, N. J.; Catalog No. S7636 or equivalent, are used along with other standard laboratory equipment as follows.

The glass slides, each having two wells therein, are thoroughly cleaned, front and back, and placed in the slide staining holder. Containers from the slide staining set are filled with distilled water(approximately 220 ml) and an equivalent number of containers are filled with 95% ethanol. The cleaned slides are soaked in the distilled water (about 3 minutes), drained on a stack of paper towels and then soaked in the ethanol (about 3 minutes). The water is changed after two uses and the ethanol after three uses. The slides are air-dried and stored, if necessary, in dust free containers until they are to be used.

A vial of the M-protein, prepared as described above, is centrifuged at 10,000 rpm for five minutes. The desired number of the slides prepared as described above are placed on a clean work surface with their well side up. An appropriate amount of the M protein preparation is applied th the well of each slide. Using one coverslip per slide, the M-Protein is spread over the surface of both wells such that the surface of each well is completely covered. The slides are then allowed to air dry.

The M Protein preparation is then fixed to the slides as follows. The slides are placed in the slide staining holder and soaked in 95% ethanol for five minutes. The ethanol bath is changed after each three uses. The slides are allowed to air dry and, thereafter, are rinsed twice with distilled water and again air dried. The slides, which are hereafter referred to as Adhesive Pretreated Specimen Slides (APT slides), are then stored at 2°–8° C. in a dessicated container, such as individual sealed foil pouches until needed for use.

The slides can be used for either frozen or paraffin embedded sections which have been formalin fixed.

A. For paraffin-embedded, formalin-fixed sections, one to three sections (4–6 microns thick) of each biopsy specimen are applied to both wells of the APT slides. The tissue mounted slides are then baked for one hour at 60° C. to fix the slides. At this point, the tissue is now permanently fixed to the slide and will remain stable at room temperature for at least one year. The remaining steps described are preparatory for a hybridization assay.

All slides, including control slides, must be deparaffinized prior to use by soaking them in the following solutions for the indicated times:

| Soak # | Reagent | Duration |
| --- | --- | --- |
| 1 | Xylene | 10 min. |
| 2 | Xylene | 2 min. |
| 3 | 100% ethanol | 1 min. |
| 4 | 100% ethanol | 1 min. |
| 5 | 90% ethanol | 1 min. |
| 6 | 70% ethanol | 1 min. |
| 7 | 50% ethanol | 1 min. |
| 8 | Deionized H$_2$O | 1 min. |

After the last soak, the slides are allowed to dry completely by incubation at 60° C. for five minutes.

To obtain maximum signal possible, formalin-fixed tissue sections should be treated with Proteinase K. Therefore, freshly diluted 1× Proteinase K solution (0.5 ml at 250 ug Proteinase K/ml) is added to each well on each slide and these slides are then incubated at 37° C. for 15 minutes. The Proteinase K solution is gently tapped off the slides which are then soaked for one minute at room temperature in each of three containers of Wash Buffer. To inactivate any peroxidase activity in the tissue section, all slides are covered with Quench Reagent (0.5 ml per well) and incubated at 37° C. for 10 minutes. The slides are then rinsed with Wash Buffer.

B. For frozen formalin-fixed sections, one to three sections (6–8 microns thick) of each biopsy specimen are applied to both wells of the APT slides. The tissue mounted slides are then baked for one hour at 60° C. to attach the tissue section to the slides. The slides are fixed by soaking in acetone for 10 minutes and then are allowed to air dry. At this point, the tissue is now permanently fixed to the slide and will remain stable at room temperature for at least one year. The remaining steps described are preparatory for a hybridization assay.

For the frozen, formalin-fixed sections, freshly prepared 10× Proteinase K solution is diluted in 20 volumes of Wash Buffer, and the resulting solution is added to each well on each slide. These slides are then incubated at 37° C. for 15 minutes. As above, the Proteinase K solution is gently tapped off the slides which are then soaked for one minute at room temperature in each of three containers of Wash Buffer.

For both paraffin embedded formalin fixed and frozen formalin fixed sections, all slides are covered with Quench Reagent (0.5 ml per well) and incubated at 37° C. for 10 minutes to inactivate any peroxidase activity in the tissue section. The slides are then rinsed with Wash Buffer, and are then dehydrated by soaking them in the following solutions for the indicated times:

| Soak # | Reagent | Duration |
| --- | --- | --- |
| 1 | Deionized H$_2$O | 1 min. |
| 2 | 50% ethanol | 1 min. |
| 3 | 70% ethanol | 1 min. |
| 4 | 100% ethanol | |

After the last soak, the slides are allowed to dry completely by incubation at 60° C. for five minutes. The slides are now ready for hybridization and staining procedures which can be performed using, for example, a PathoGene DNA Probe Assay Kit for identification of Human Papilloma Virus (HPV).

What is claimed is:

1. A method of treating a sample suspected of containing a target polynucleotide so as to adhere the sample to a substrate under conditions suitable for nucleic acid hybridization, which method comprises:
   (a) depositing onto said substrate an adhesive composition which comprises an isolate of a naturally occurring mussel adhesive protein;
   (b) adhering said sample onto at least a portion of the substrate to which said adhesive composition has been deposited; and
   (c) treating said adhered sample so as to prepare said sample for nucleic acid hybridization.

2. The method of claim 1 wherein said target polynucleotide is of human, animal, microbial, plant or viral origin.

3. The method of claim 1 wherein said isolate comprises an acid-soluble protein.

4. The method of claim 1 wherein said sample comprises cells.

5. The method of claim 4 wherein said treating step comprises disrupting the cells thereof so as to expose the nucleic acid contents for hybridization.

6. The method of claim 4 wherein said treating step comprises fixing the cells in said sample and exposing said sample to a reagent selected from formamide and a strong acid.

7. The method of claim 1 wherein said sample comprises a tissue.

8. The method of claim 4 or 7 wherein said treating step comprises contacting said sample with a proteinase.

9. The method of claim 7 wherein said treating step comprises disrupting the tissue thereof so as to expose the nucleic acid contents for hybridization.

10. The method of claim 7 wherein said treating step comprises fixing the tissue in said sample and exposing said sample to a reagent selected from formamide and a strong acid.

11. A nucleic acid hybridization assay for detecting a target polynucleotide in a sample, which method comprises:

(a) depositing onto a substrate an adhesive composition comprising an isolate of a naturally occurring mussel adhesive protein;

(b) adhering a sample suspected of containing said target polynucleotide onto a portion of the substrate to which said adhesive composition has been deposited;

(c) contacting said adhered sample under hybridization assay conditions with a composition comprising a detectable labeled oligo-or or polynucleotide probe specifically hybridizable with a portion of said target polynucleotide; and (d) detecting any response thereto.

12. The method of claim 11 wherein said sample comprises cells.

13. The method of claim 12 wherein said cells are derived from a human, animal, microbe or plant.

14. The method of claim 11 wherein said isolate comprises an acid-soluble protein.

15. The method of claim 11 wherein said target polynucleotide is of human, animal, microbial, plant or viral origin.

16. The method of claim 11 wherein said substrate comprises a microscope slide.

17. The method of claim 11 wherein said detectable label is selected from the group consisting of avidin, streptavidin, biotin, iminobiotin, an electron dense component, a magnetic component, an enzyme, a hormone component, a radioactive component, a metal-containing component, a fluorescing component, an antigen component, an antibody component, or combinations thereof.

18. The method of claim 11 wherein said sample comprises a tissue.

19. The method of claim 18 wherein said tissue is derived from a human, animal or plant.

20. A nucleic acid hybridization assay for a target polynucleotide in a sample, which method comprises:

(a) depositing onto a substrate an adhesive composition comprising an isolate of a naturally occurring mussel adhesive protein;

(b) adhering a first composition comprising an oligo- or polynucleotide specifically hybridizable with a first portion of said target polynucleotide onto said substrate to which said adhesive composition has been deposited;

(c) contacting said adhered first composition under hybridization assay conditions with a sample suspected of containing said target polynucleotide and a composition comprising a detectable labeled oligo- or polynucleotide specifically hybridizable with a second portion of said target polynucleotide; and (d) detecting any response thereto.

21. The method of claim 20 wherein said sample comprises cells.

22. The method of claim 21 wherein said cells are derived from a human, animal, microbe or plant.

23. The method of claim 20 wherein said isolate comprises an acid-soluble protein.

24. The method of claim 20 wherein said target polynucleotide is of human, animal, microbial, plant or viral origin.

25. The method of claim 20 wherein said substrate comprises a microscope slide.

26. The method of claim 20 wherein said detectable label is selected from the group consisting of avidin, streptavidin, biotin, iminobiotin, an electron dense component, a magnetic component, an enzyme, a hormone component, a radioactive component, a metal-containing component, a fluorescing component, an antigen component, an antibody component, or combinations thereof.

27. The method of claim 20 wherein said sample comprises a tissue.

28. The method of claim 27 wherein said tissue is derived from a human, animal or plant.

29. A nucleic acid hybridization assay kit for detecting a target polynucleotide in a sample, which kit comprises:

(a) at least one analytical element having thereon an adhesive composition comprising an isolate of a naturally occurring mussel adhesive protein, said composition being capable of adhering a sample suspected of containing said target polynucleotide, or an oligo- or polynucleotide specifically hybridizable with a portion of said target polynucleotide; and (b) a container having therein a composition comprising a detectable labeled oligo- or polynucleotide probe which is specifically hybridizable with a portion of said target polynucleotide and which produces directly or indirectly a detectable response when hybridized with said target.

30. The kit of claim 29 wherein said isolate comprises an acid-soluble protein.

31. A nucleic acid hybridization kit for detecting a target polynucleotide in a sample, which kit comprises:

(a) at least one analytical element having thereon an adhesive composition comprising an isolate of a naturally occurring mussel adhesive protein, said composition having adhered thereto an oligo- or polynucleotide specifically hybridizable with a first portion of said target polynucleotide; and (b) a container having therein a detectable labeled oligo- or polynucleotide specifically hybridizable with a second portion of said target polynucleotide.

32. The kit of claim 31 wherein said isolate comprises an acid-soluble protein.

* * * * *